United States Patent [19]

Ernst et al.

[11] Patent Number: 5,210,314
[45] Date of Patent: May 11, 1993

[54] PREPARATION OF CANTHAXANTHIN AND ASTAXANTHIN

[75] Inventors: Hansgeorg Ernst, Speyer; Joachim Paust; Werner Hoffmann, both of Neuhofen, all of Fed. Rep. of Germany

[73] Assignee: BASF Aktiengesellschaft, Ludwigshafen, Fed. Rep. of Germany

[21] Appl. No.: 695,336

[22] Filed: Apr. 29, 1991

[30] Foreign Application Priority Data

May 3, 1990 [DE] Fed. Rep. of Germany ....... 4014203

[51] Int. Cl.$^5$ ...................... C07C 45/61; C07C 45/65
[52] U.S. Cl. .................... 568/345; 568/346; 568/377; 568/378
[58] Field of Search ............... 568/345, 377, 378, 346

[56] References Cited

U.S. PATENT DOCUMENTS

| | | | |
|---|---|---|---|
| 3,006,939 | 10/1961 | Pommer et al. | 260/413 |
| 4,088,689 | 5/1978 | Rosenberger | 260/586 R |
| 4,098,827 | 7/1978 | Rosenberger | 568/824 |
| 4,156,090 | 5/1979 | Kienzle | 560/61 |
| 4,245,109 | 1/1981 | Mayer et al. | 560/61 |
| 4,283,559 | 8/1981 | Broger et al. | 568/11 |
| 4,585,885 | 4/1986 | Bernhard et al. | 556/436 |

OTHER PUBLICATIONS

J. Org. Chem. 47 (1982) pp. 2130–2134.

*Primary Examiner*—Jose G. Dees
*Assistant Examiner*—B. Frazier
*Attorney, Agent, or Firm*—Keil & Weinkauf

[57] ABSTRACT

A process for preparing canthaxanthin (Ia) and astaxanthin (Ib) of the formula I where R is H (a) or OH (b), comprises reacting a tertiary alcohol of the formula II

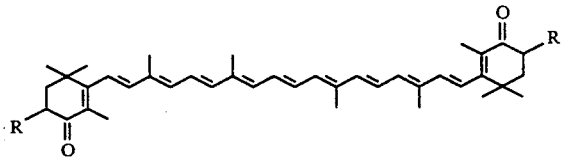

where R is H (a) or OH (b), with trifluoroacetic acid, reacting the resulting novel trifluoroacetate of the formula III

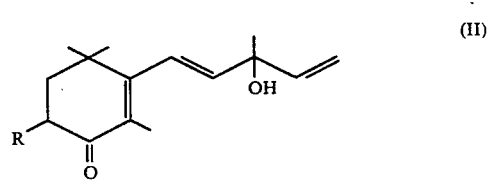

with triphenylphosphine, and reacting the resulting novel triphenylphosphonium trifluoroacetate of the formula IV

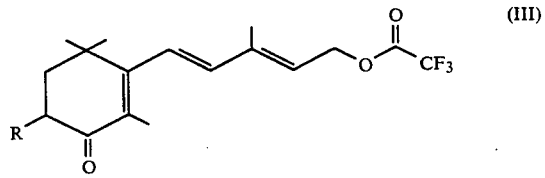

with 2,7-dimethyl-2,4,6-octatriene-1,8-dial under the conditions of a Wittig synthesis. The present invention also relates to the novel trifluoroacetates of the formula III and the corresponding triphenylphosphonium trifluoroacetates of the formula IV.

8 Claims, No Drawings

PREPARATION OF CANTHAXANTHIN AND ASTAXANTHIN

The present invention relates to a novel process for preparing the carotenoids canthaxanthin (Ia) and astaxanthin (Ib) which are in demand.

A synthesis designed for these two carotenoids which has been described several times is based on double Wittig condensation of an appropriate $C_{15}$ phosphonium salt with the symmetrical $C_{10}$ dialdehyde 2,7-dimethyl-2,4,6-octatriene-1,8-dial.

The $C_{15}$ phosphonium salts employed in the prior art are the halides of the following formula, where the anion used is, in particular, the bromide.

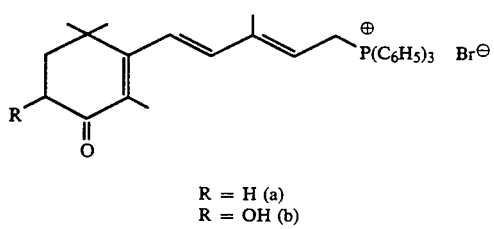

R = H (a)
R = OH (b)

The phosphonium salts suitable as $C_{15}$ synthons for canthaxanthin and astaxanthin using the $C_{15}+C_{10}+C_{15}$ synthesis principle described above are prepared by reacting the corresponding allyl bromides of the formula

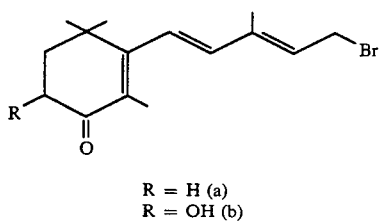

R = H (a)
R = OH (b)

with triphenylphosphine.

The said allyl bromides are obtainable by halogenation, with allyl rearrangement, of the tertiary alcohols of the formula II,

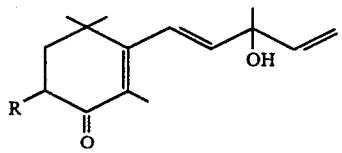

where R is H (a) or OH (b).

This synthetic route, which has been described in the literature several times, has serious disadvantages for industrial use because of the technical demands of the process and the economics.

Thus, for example, the conversion of the tertiary alcohol of the formula IIb into the corresponding allyl bromide with 63% strength aqueous hydrobromic acid must be carried out at low temperature (at −20° C. to −10° C. according to EP 101 597; at +5° C. according to EP 5749 and at 0° C. according to Helv. chim. acta 64 (1981) 2430), and a considerable excess of hydrogen bromide (2.5-4 equivalents) is necessary. According to the statements in Helv. chim. acta 64 (1981) 2430 and 2440 the reaction must be carried out at low temperature and very rapidly in order to avoid decomposition of the rather unstable allyl bromide and to suppress rearrangement of the α-hydroxy ketone to the diosphenol.

In addition, butylene oxide must be added several times during further processing of the allyl bromide to remove traces of acid.

In the prior art preparation of canthaxanthin, the tertiary alcohol of the formula IIa is converted by treatment with phosphorus tribromide in an inert organic solvent into the corresponding allyl bromide, from which the corresponding phosphonium salt is obtained by reaction with triphenylphosphine (DE-A 2 801 908). In this case too a considerable excess ($\geq 3$ equivalents) of the costly halogenating agent must be used. An alternative to the bromination with phosphorus tribromide and subsequent reaction with triphenylphosphine is to prepare the triphenylphosphonium bromide directly from the tertiary alcohol of the formula IIa by reaction with triphenylphosphine hydrobromide (cf. DE-A 2 801 908). However, this reagent has to be prepared in a separate stage from triphenylphosphine and HBr and likewise has to be used in considerable excess.

The best method for preparing the $C_{15}$ triphenylphosphonium salt is stated in J. Org. Chem. 47 (1982) 2133 to be the reaction of the tertiary alcohol of the formula IIa with triphenylphosphine hydrobromide, the latter being used in an excess of 17 mol %.

Thus, the disadvantages of the prior art processes are that the halogen reacting agents which have to be used for converting the tertiary alcohols of the formula II into the corresponding triphenylphosphonium bromides have to be employed in considerable excess and are costly and involve some technical problems. A further problem in the preparation of astaxanthin is the low stability of the corresponding allyl bromide.

It is an object of the present invention to develop a process for preparing canthaxanthin and astaxanthin which does not have the disadvantages of the prior art.

We have found that this object is achieved in that, surprisingly, the tertiary alcohols of the formula II can be converted smoothly by treatment with trifluoroacetic acid into the novel trifluoroacetates of the formula III and the latter can subsequently be converted into the phosphonium salts of the formula IV by reaction with triphenylphosphine. The procedure is identical for both precursors, which is a further considerable industrial advantage for this novel process.

Hence the present invention relates to a process for preparing canthaxanthin (Ia) and astaxanthin (Ib) of the formula I

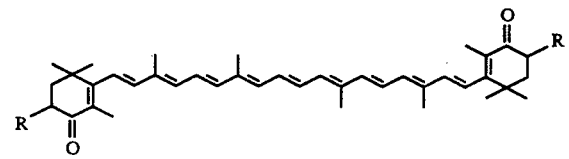

where R is H (a) or OH (b), which comprises
A. reacting a tertiary alcohol of the formula II

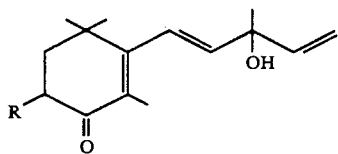

where R is H (a) or OH (b), with trifluoroacetic acid,
B. reacting the resulting novel trifluoroacetate of the formula III

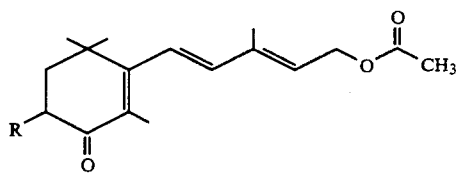

with triphenylphosphine, and c. reacting the resulting novel triphenylphosphonium trifluoroacetate of the formula IV

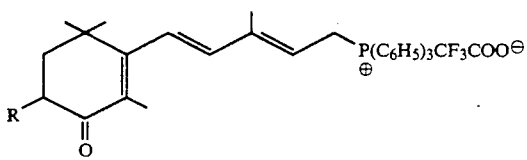

where R is H (a) or OH (b),
with 2,7-dimethyl-2,4,6-octatriene-1,8-dial under the conditions of a Wittig synthesis.

The present invention also relates to the novel intermediates of the formulae III and IV, which make the advantageous new process possible.

The reaction of the tertiary alcohols of the formula II with trifluoroacetic acid is generally carried out in an inert organic solvent such as methylene chloride, 1,2-dichloroethane or ethyl acetate at from about 0° C. to +50° C., preferably 10°-30° C., and in particular at room temperature. Only 1.0–1.05 equivalents of trifluoroacetic acid based on the alcohols of the formula II are required. The reaction takes place smoothly to give good yields of the novel trifluoroacetates of the formula III without esterification of the secondary hydroxyl group of IIIb and without the danger of the α-ketol being rearranged to the diosphenol.

The crude trifluoroacetates of the formula III can be directly converted into the phosphonium salts of the formula IV, for example by heating with a triarylphosphine, especially triphenylphosphine, in an inert organic solvent such as toluene, ethyl acetate or methylene chloride. This reaction is carried out particularly straightforwardly by heating the crude trifluoroacetate with triphenylphosphine in the absence of a solvent.

In general, from 1.0 to 1.2 moles of triphenylphosphine are used per mole of trifluoroacetate of the formula III. The reaction is generally carried out at from room temperature to the reflux temperature of the solvent, preferably at from about 50° to 100° C. When the reaction is carried out without solvent at from 80° to 100° C., for example, it takes about 15 to 30 minutes.

The resulting crude phosphonium salt of the formulae IV can be purified by precipitation from a suitable organic solvent such as methyl tert-butyl ether (MTB) or diisopropyl ether.

Reaction of the phosphonium salts of the formulae IVa and IVb with the $C_{10}$ dialdehyde 2,7-dimethyl-2,4,6-octatriene-1,8-dial under the conditions typically used for such Wittig condensations gives the carotenoids canthanxanthin Ia and astaxanthin Ib, respectively, in good yields.

Further details of the conditions for Wittig reactions may be found, for example, in J. Org. Chem. 47 (1982) 2130–2134 and Helv. Chim. Acta 64 (1981) 2436 et seq.

The examples which follow are intended to illustrate the process according to the invention.

EXAMPLE 1

A. Preparation of 5-(2,6,6-trimethyl-3-oxo-1-cyclohexen-1-yl)-3-methyl-2,4-pentadien-1-ol trifluoroacetate (IIIa)

10.0 g (42.7 mmol) of 5-(2,6,6-trimethyl-3-oxo-1-cyclohexen-1-yl)-3-methyl-3-hydroxy-1,4-pentadiene (IIa) were dissolved in 40 ml of methylene chloride and, at 0° C., 4.4 ml (43.2 mmol) of trifluoroacetic acid (D 1.12) were added dropwise. The reaction mixture was then allowed to reach room temperature (RT) and was stirred at RT for 3 hours (h).

The mixture was then poured into water. The organic phase was separated off, and the aqueous phase was extracted with methylene chloride. The combined organic phases were washed with dilute sodium bicarbonate solution and dried over sodium sulfate. The solvent was stripped off in a rotary evaporator to yield 12 g of the trifluoroacetate IIIa as a reddish oil.

IR spectrum (film): 1784 $cm^{-1}$ (vs), 1665 $cm^{-1}$ (s), 1217 $cm^{-1}$ (vs), 1168 $cm^{-1}$ (vs).

B. Preparation of 5-(2,6,6-trimethyl-3-oxo-1-cyclohexen-1-yl)-3-methyl-2,4-pentadien-1-yltriphenylphosphonium trifluoroacetate (IVa)

The crude trifluoroacetate IIIa was stirred with 9.5 g of triphenylphosphine in an oil bath preheated to 100°–120 C. for 30 minutes (min). The residue was allowed to cool and the crude phosphonium salt was dissolved in methylene chloride. This solution was added dropwise to methyl tert-butyl ether (MTB) to precipitate the triphenylphosphonium salt IVa as white crystals of melting point 150°–154° C.

Calculated for $C_{35}H_{36}PO_3F_3$: C 71.0% H 6.1% P 5.2% O 8.1% F 9.6%

Analytical findings: C 70.6% H 5.9% P 5.1% F 9.5%

C. Preparation of canthaxanthin (Ia)

5.3 g of the phosphonium salt IVa and 500 mg of 2,7-dimethyl-2,4,6-octatriene-1,8-dial were dissolved in 25 ml of methylene chloride. The mixture was cooled to 0° C. and 1.6 g of a 30% strength methanolic solution of sodium methylate were added dropwise, and then the mixture was allowed to reach RT and was stirred for 2 h. The mixture was then poured into water. The organic phase was separated off, and the aqueous phase was extracted with methylene chloride. The combined organic phases were dried over sodium sulfate and concentrated in a rotary evaporator. The residue was taken up in 20 ml of methanol and refluxed for 30 min, then cooled to 0° C., and the precipitated canthaxanthin was filtered off.

Yield: 1.1 g of canthaxanthin

A further 0.4 g of canthaxanthin was obtained by column chromatography of the mother liquor.

EXAMPLE 2

A. Preparation of 5-(2,6,6-trimethyl-3-oxo-4-hydroxy-1-cyclohexen-1-yl)-3-methyl-2,4-pentadiene-1-ol trifluoroacetate (IIIb)

8 g (32 mmol) of 5-(2,6,6-trimethyl-3-oxo-4-hydroxy-1-cyclohexen-1-yl)-3-methyl-3-hydroxy-1,4-pentadiene (IIb) were dissolved in 25 ml of methylene chloride. 3.7 g (32.5 mmol) of trifluoroacetic acid were added dropwise at 0° C. The mixture was allowed to reach RT and was stirred at RT for 5 h and was then poured into dilute sodium bicarbonate solution. The organic phase was separated off, and the aqueous phase was extracted with methylene chloride. The combined organic phases were washed with dilute bicarbonate solution and dried over sodium sulfate. The solvent was stripped off in a rotary evaporator to yield 9–10 g of the trifluoroacetate IIIb as a crude oil.

IR spectrum (film): 3500 cm$^{-1}$ (broad), 1784 cm$^{-1}$ (vs), 1670 cm$^{-1}$ (s), 1221 cm$^{-1}$ (s), 1168 cm$^{-1}$ (vs), 1149 cm$^{-1}$ (vs).

B. Preparation of 5-(2,6,6-trimethyl-3-oxo-4-hydroxy-1-cyclohexen-1-yl)-3-methyl-2,4-pentadien-1-yltriphenylphosphonium trifluoroacetate (IVb)

1.3 g of the resulting crude trifluoroacetate IIIb were stirred with 1.0 g of triphenylphosphine in an oil bath preheated to 100° C. for 30 min. The residue was allowed to cool, and the crude phosphonium salt was dissolved in ethyl acetate and reprecipitate by adding this solution dropwise to MTB. The precipitate was separated off and dried under reduced pressure. 1.3–1.4 g of the triphenylphosphonium salt IVb were obtained as a pale yellow foam.

Reprecipitation of an ethyl acetate solution by dropwise addition to MTB yielded the phosphonium salt IVb as colorless crystals.

Melting point: 147°–148° C., fluorine content, calculated: 9.4%, found: 9.5%.

C. Preparation of astaxanthin (Ib)

8.4 g of the crystalline phosphonium salt IVb and 760 mg of 2,7-dimethyl-2,4,6-octatriene-1,8-dial were dissolved in 33 ml of methylene chloride. The mixture was cooled to 0° C. and 2.24 g of a 30% strength methanolic solution of sodium methylate were added dropwise, and the mixture was allowed to reach RT and was stirred for 3½ h. The reaction mixture was then poured into water. The organic phase was separated off, and the aqueous phase was extracted with methylene chloride. The combined organic phases were washed with water, dried over sodium sulfate and concentrated in a rotary evaporator. Pure astaxanthin was obtained by purification of the crude product by column chromatography.

Yield: 2.3 g of astaxanthin.

We claim:

1. A process for preparing canthaxanthin (Ia) and astaxanthin (Ib) of the formula I

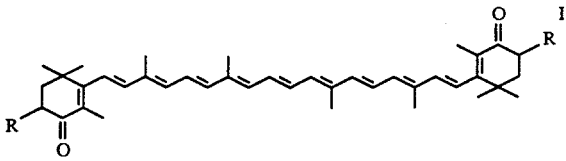

where R is H (a) or OH (b), which comprises
A. reacting a tertiary alcohol of the formula II

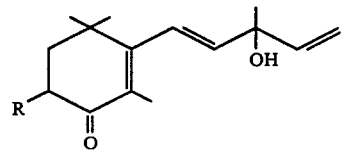

where R is H (a) or OH (b), with trifluoroacetic acid at a temperature of about 0° to 50° C.,
B. reacting the resulting trifluoroacetate of the formula III

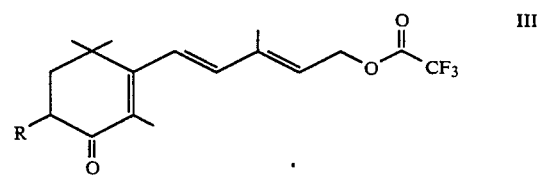

with triphenylphosphine at a temperature of about 50° to 100° C., and
C. reacting the resulting triphenylphosphonium trifluoroacetate of the formula IV

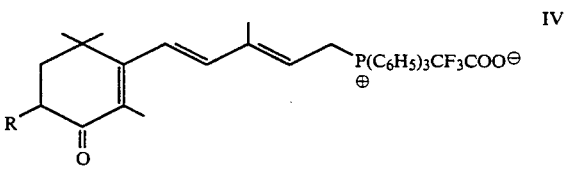

where R is H (a) or OH (b), with 2,7-dimethyl-2,4,6-octatriene-1,8-dial, under the conditions of a Wittig synthesis.

2. The process of claim 1, wherein R is H.
3. The process of claim 1, wherein R is OH.
4. The process of claim 1 wherein a tertiary alcohol of the formula II is reacted with trifluoroacetic acid at a temperature of from 10° to 30° C.
5. The process of claim 1, wherein from 1.0 to 1.05 equivalents of trifluoroacetic acid are used based on the alcohol of the formula II.
6. The process of claim 1, wherein from 1.0 to 1.2 moles of triphenylphosphine are used per mole of trifluoroacetate of the formula III.
7. The process of claim 1, wherein the reaction of triphenylphosphine and trifluoroacetate of the formula III is carried out at from about 80° to 100° C.
8. The process of claim 1, wherein from 1.0 to 1.05 equivalents of trifluoroacetic acid are used based on the alcohol of the formula II and wherein from 1.0 to 1.2 moles of triphenylphosphine are used per mole of trifluoroacetate of the formula III.

* * * * *